United States Patent
Ho

(10) Patent No.: US 11,453,009 B2
(45) Date of Patent: Sep. 27, 2022

(54) TEST TUBE

(71) Applicant: AI Bioelectronic Healthtech Co., Ltd., Taoyuan (TW)

(72) Inventor: Yen-Yi Ho, Taoyuan (TW)

(73) Assignee: AI Bioelectronic Healthtech Co., Ltd., Taoyuan (TW)

( * ) Notice: Subject to any disclaimer, the term of this patent is extended or adjusted under 35 U.S.C. 154(b) by 255 days.

(21) Appl. No.: 17/006,994

(22) Filed: Aug. 31, 2020

(65) Prior Publication Data
US 2021/0138456 A1    May 13, 2021

(30) Foreign Application Priority Data
Nov. 8, 2019    (TW) .................................. 108140683

(51) Int. Cl.
*B01L 3/00*    (2006.01)
*H04L 67/12*   (2022.01)

(52) U.S. Cl.
CPC ..... *B01L 3/5082* (2013.01); *B01L 2200/0689* (2013.01); *B01L 2200/141* (2013.01); *B01L 2200/143* (2013.01); *B01L 2200/147* (2013.01); *B01L 2300/021* (2013.01); *B01L 2300/023* (2013.01); *B01L 2300/046* (2013.01); *B01L 2300/0627* (2013.01); *B01L 2300/12* (2013.01); *H04L 67/12* (2013.01)

(58) Field of Classification Search
CPC ................................................ B01L 2300/021
See application file for complete search history.

(56) References Cited

U.S. PATENT DOCUMENTS

2012/0252134 A1    10/2012   Galiano
2019/0017008 A1     1/2019   Pahara et al.
2019/0331702 A1*   10/2019   Menhardt ........ G01N 35/00613

FOREIGN PATENT DOCUMENTS

| CN | 200942340 Y    | 9/2007 |
| CN | 209117584 U    | 7/2019 |
| CN | 110099245 A    | 8/2019 |
| WO | WO2006027054 A1 | 3/2006 |
| WO | WO2011073768 A1 | 6/2011 |

OTHER PUBLICATIONS

Park YR, Lee E, Na W, Park S, Lee Y, Lee JH Is Blockchain Technology Suitable for Managing Personal Health Records? Mixed-Methods Study to Test Feasibility J Med Internet Res 2019;21(2):e12533 (Year: 2019).*

* cited by examiner

*Primary Examiner* — Christopher Adam Hixson
(74) *Attorney, Agent, or Firm* — Alan D. Kamrath; Karin L. Williams; Mayer & Williams PC

(57) ABSTRACT

A test tube for containing a liquid and electrically connected to a blockchain network is provided. The test tube includes a tube body, a cover, at least one overlay unit, a chipset and a detection module. The tube body contains the liquid. The cover is disposed at the top of the tube body and including at least one drip tube. The overlay unit covers the drip tube. The chipset is disposed on the tube body and includes a blockchain tracer. The blockchain tracer records the source of the liquid and a transportation history of the test tube in the blockchain network for tracing. The detection module is disposed on the tube body and electrically connected to the chipset, for measuring a liquid property of the liquid.

10 Claims, 4 Drawing Sheets

TEST TUBE

BACKGROUND OF THE INVENTION

Field of the Invention

The present disclosure relates to test tubes; more particularly, the present disclosure relates to a test tube capable of being hermetically sealed and conveniently tracing and detecting the source of a liquid contained therein.

Description of the Prior Art

A test tube is a common test tool which essentially comprises a tube body made of glass. The glass tube body contains a liquid to be tested. However, the mouth of the glass tube body is exposed. Consequently, the odds are that the liquid in the glass tube body will be contaminated by microorganisms from outside.

Furthermore, conventional test tubes and test systems confirm whether a liquid under test carries virus but cannot trace the source of the liquid under test, not to mention investigate into the source of the liquid under test. Therefore, it is imperative to provide a test tube capable of being hermetically sealed and conveniently tracing and detecting the source of a liquid contained therein.

SUMMARY OF THE INVENTION

It is an objective of the present disclosure to provide a test tube capable of being hermetically sealed and conveniently tracing and detecting the source of a liquid contained therein.

In order to achieve the above and other objectives, the present disclosure provides a test tube for containing a liquid and electrically connected to a blockchain network. The test tube includes a tube body, a cover, at least one overlay unit, a chipset and a detection module. The tube body contains the liquid. The cover is disposed at the top of the tube body. The cover includes at least one drip tube. The overlay unit covers a drip tube. The chipset is disposed on the tube body. The chipset includes a blockchain tracer. The blockchain tracer records the source of the liquid and a transportation history of the test tube in the blockchain network for tracing. The detection module is disposed on the tube body and electrically connected to the chipset, for measuring a liquid property of the liquid.

According to an embodiment of the present disclosure, the test tube further includes a bottom supporting element, and the bottom supporting element is disposed at the bottom of the tube body.

According to an embodiment of the present disclosure, the chipset further includes a positioning element for positioning the test tube in place.

According to an embodiment of the present disclosure, the chipset further includes a temperature detecting element for detecting the temperature of the test tube.

According to an embodiment of the present disclosure, the chipset further comprises an RFID tag, and the RFID tag records information of the test tube by radio frequency identification (RFID).

According to an embodiment of the present disclosure, the test tube further includes a wireless module disposed at the tube body and electrically connected to the chipset, the detection module and an external computer.

According to an embodiment of the present disclosure, the test tube further includes a battery disposed at the tube body and adapted to provide power to the chipset, the detection module and the wireless module.

According to an embodiment of the present disclosure, the tube body further includes an injection needle, and the bottom supporting element further includes a supporting tube for containing the injection needle.

According to an embodiment of the present disclosure, the tube body is made of biodegradable plastic.

According to an embodiment of the present disclosure, the positioning element is a global positioning system chip.

DETAILED DESCRIPTION OF THE EMBODIMENTS

The implementation of the present disclosure is illustrated by preferred, specific embodiments to enable persons skilled in the art to easily understand the other advantages and effects of the present disclosure by referring to the disclosure contained therein.

Figure 1:
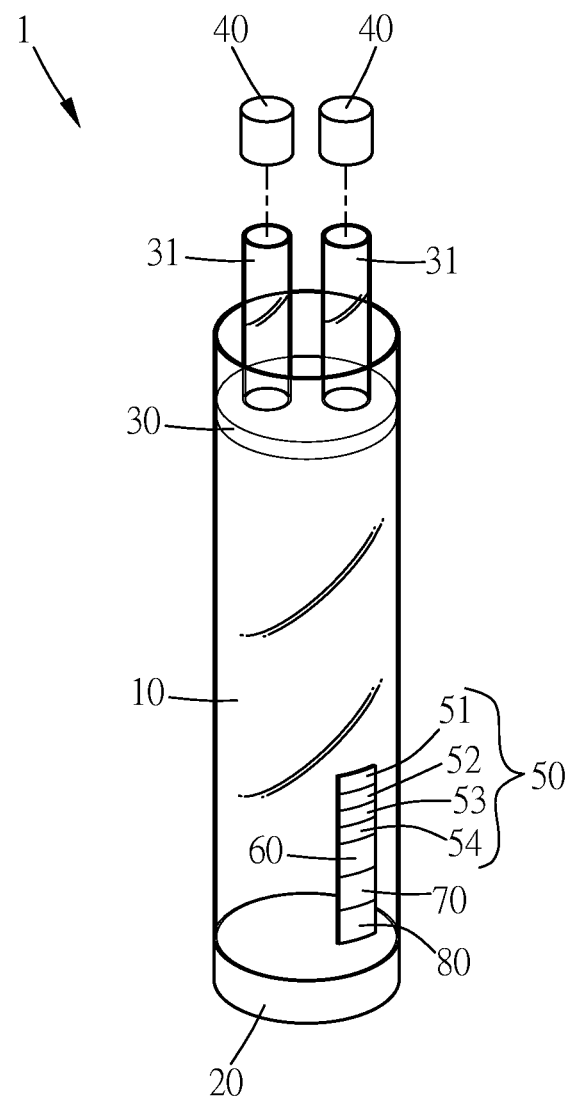
FIG. 1 is a schematic view of a test tube according to the first embodiment of the present disclosure.
Figure 2:
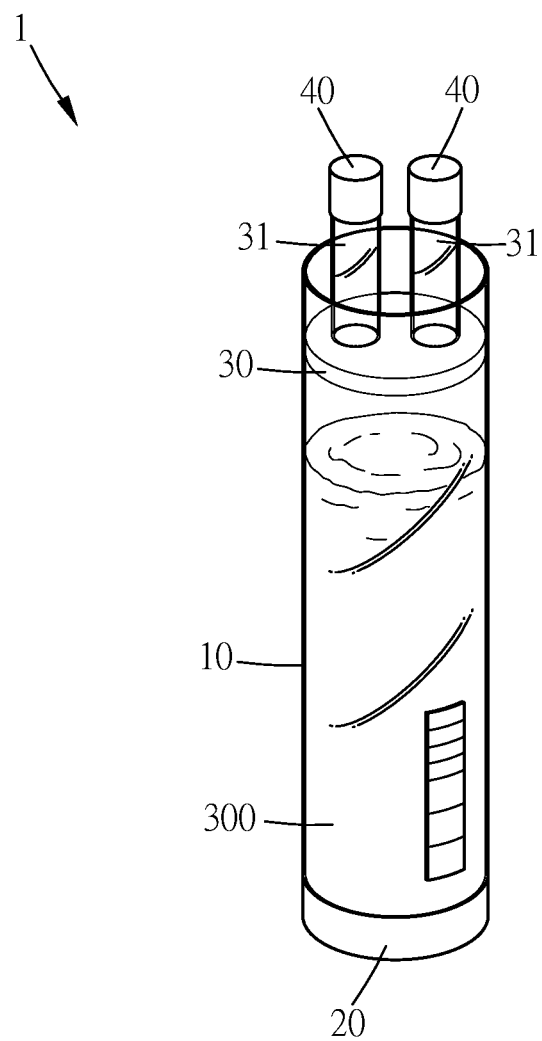
FIG. 2 is a schematic view of the test tube filled with a liquid and packaged according to the first embodiment of the present disclosure.
Figure 3:
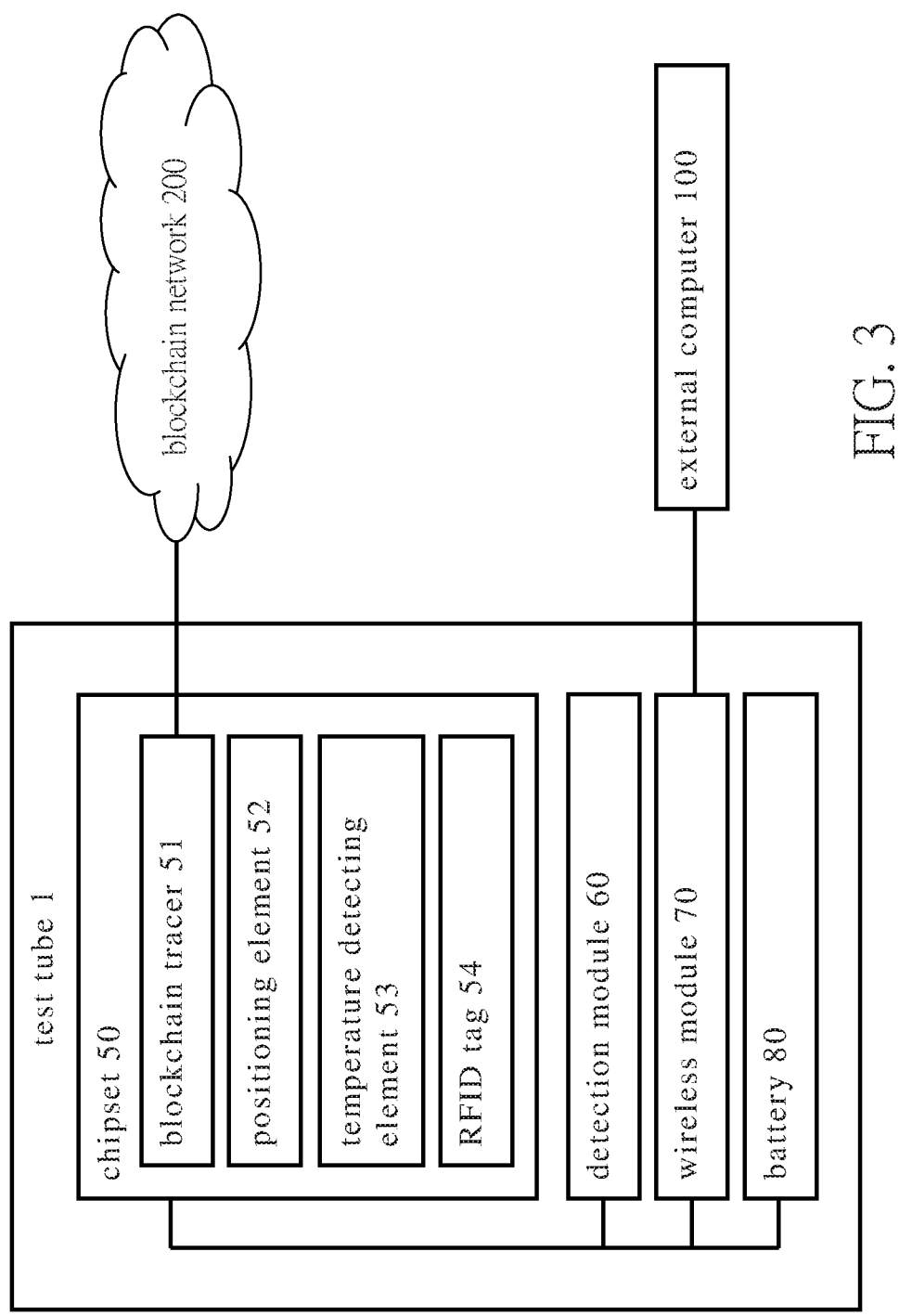
FIG. 3 is a block diagram of the test tube, an external network and a blockchain computer according to the first embodiment of the present disclosure.

Referring to FIG. 1 through FIG. 3, a test tube is provided in the first embodiment of the present disclosure. FIG. 1 is a schematic view of a test tube according to the first embodiment of the present disclosure. FIG. 2 is a schematic view of the test tube filled with a liquid and packaged according to the first embodiment of the present disclosure. FIG. 3 is a block diagram of the test tube, an external network and a blockchain computer according to the first embodiment of the present disclosure.

As shown in FIG. 1 through FIG. 3, in the first embodiment of the present disclosure, a test tube 1 contains a liquid 300 and is electrically connected to a blockchain network 200. The test tube 1 is hermetically sealed to prevent contamination and is capable of tracing and detecting the source of the liquid 300 conveniently. The test tube 1 is electrically connected to an external computer 100 to transmit information pertaining to the test tube 1 and the liquid 300 therein to the external computer 100. The test tube 1 includes a tube body 10, a bottom supporting element 20, a cover 30, two overlay units 40, a chipset 50, a detection module 60, a wireless module 70 and a battery 80.

In the first embodiment of the present disclosure, the tube body 10 contains the liquid 300. The tube body 10 is made of biodegradable plastic. The biodegradable plastic is made from a biodegradable material, such as starch, polylactide and fibrous protein. Therefore, the tube body 10 is biodegradable and thus environment-friendly.

In the first embodiment of the present disclosure, the bottom supporting element 20 is, for example, a base made of rubber, and is disposed at the bottom of the tube body 10. The bottom supporting element 20 ensures that the tube body 10 is upright and prevents the bottom of the tube body 10 from hitting any external object directly and thus rupturing.

In the first embodiment of the present disclosure, the cover 30 is disposed at the top of the tube body 10. The cover 30 includes two drip tubes 31. The cover 30 covers the mouth at the top of the tube body 10 to reduce the area of exposure of the mouth. The liquid 300, which is to be detected, flows into the tube body 10 from the two drip tubes 31. However, the number of the drip tubes 31 is not limited to two but is subject to changes as needed.

In the first embodiment of the present disclosure, the two overlay units 40 are, for example, covers or corks made of soft plastic, and are intended to cover the two drip tubes 31, respectively, such that the interior of the tube body 10 forms a closed system, so as to shut out external microorganisms to ensure that the liquid 300 in the tube body 10 will not be denatured. However, the number of the overlay units 40 is not limited to two but is subject to changes to match the drip tubes 31 in quantity.

In the first embodiment of the present disclosure, the chipset 50 is disposed on the tube body 10. The chipset 50 includes a blockchain tracer 51, a positioning element 52, a temperature detecting element 53 and an RFID tag 54. The blockchain tracer 51 is a computation chip and is electrically connected to the blockchain network 200. The blockchain tracer 51 records the source and history of the liquid 300 in the blockchain network 200. The blockchain tracer records and traces information of the liquid, such that the information of the liquid cannot be tampered with. Therefore, the blockchain tracer 51 is effective in recording and tracing the transportation history of the test tube 1. According to an embodiment of the present disclosure, the source of the liquid 300 is, for example, blood or urine attributed to a subject receiving a health checkup, whereas the transportation history includes the venue of the health checkup, the medical institution carrying out the health checkup, and the procedure of preserving the test tube 1 and transporting the test tube 1. Furthermore, information pertaining to the transportation history of the test tube 1 is entered into the blockchain tracer 51 with the external computer 100, and then the blockchain tracer 51 records the transportation history of the test tube 1 in the blockchain network 200. Thus, related information is recorded and traced with the blockchain tracer and thus cannot be tampered with. Therefore, the source and transportation history of the liquid 300 in the test tube 1 can be clearly recorded and managed.

The positioning element 52 is a global positioning system chip. The positioning element 52 positions the test tube 1 in place to confirm the current position of the test tube 1. The temperature detecting element 53 is a chip capable of temperature sensing to detect the temperature of the test tube 1 and thus determine whether the temperature of the test tube 1 is appropriate, thereby preventing the liquid 300 from being denatured in an overheated environment. The RFID tag 54 records the information of the test tube 1, such as the capacity of the test tube 1, the expiry date of the tube body 10, the identity of the subject who is the owner of the liquid 300 in the test tube 1, the date of test, and the venue of test, by radio frequency identification (RFID). The information to be recorded by the RFID tag 54 is entered with the external computer 100. However, the information of the test tube 1 is not limited thereto but is subject to changes as needed.

In the first embodiment of the present disclosure, the detection module 60 is disposed at the tube body 10 and electrically connected to the chipset 50. The detection module 60 is a chip capable of measuring liquid property to measure at least one liquid property of the liquid 300. The liquid property includes, for example, the adhesiveness, pH, specific weight, permeability, and osmotic pressure of the liquid. With the detection module 60 being capable of measuring liquid property, it is feasible to determine whether the liquid 300 is in good condition or is denatured. However, the liquid property which can be measured with the detection module 60 is not limited thereto but is subject to changes as needed.

In the first embodiment of the present disclosure, the wireless module 70 is, for example, a network chip. The wireless module 70 is disposed at the tube body 10 and electrically connected to the chipset 50, detection module 60 and external computer 100. The wireless module 70 transmits information detected by the chipset 50 and detection module 60 to the external computer 100, such that medical staff can operate the external computer 100 to access the information of the liquid 300 contained in the test tube 1, such as liquid source, liquid history and liquid property.

In the first embodiment of the present disclosure, the battery 80 is disposed at the tube body 10 and adapted to provide power to the chipset 50, detection module 60 and wireless module 70, so as to ensure that the chipset 50, detection module 60 and wireless module 70 can function well.

As shown in FIG. 1 through FIG. 3, the test tube 1 of the present disclosure contains, for example, the liquid 300 (for example, a subject's blood) under test during a health checkup. The liquid 300 flows into the tube body 10 via the drip tube 31. The detection module 60 measures the liquid property of the liquid 300, for example, the adhesiveness, pH, specific weight, permeability, and osmotic pressure of the liquid. With the detection module 60 being capable of measuring liquid property, it is feasible to determine whether the liquid 300 is in good condition or is denatured.

The positioning element 52 positions the test tube 1 in place to confirm the current position of the test tube 1, so as to prevent the test tube 1 from getting lost. The temperature detecting element 53 is a chip capable of temperature sensing to detect the temperature of the test tube 1 and thus determine whether the temperature of the test tube 1 is appropriate, thereby protecting the quality of the liquid 300 against overheating.

Medical Staff operates the external computer 100 to access the wireless module 70 of the test tube 1 to enter into the RFID tag 54 the information of the test tube 1, such as the capacity of the test tube 1, the expiry date of the tube body 10, the identity of the subject who is the owner of the liquid 300 in the test tube 1, the date of test, and the venue of test. After that, the medical staff use an RFID reader to read the information recorded in the RFID tag 54 so as to access information pertaining to the test tube 1 and liquid 300 quickly.

Furthermore, the medical staff enters transportation history information into the blockchain tracer 51 with the external computer 100, and then the blockchain tracer 51 records the transportation history information in the blockchain network 200. With the blockchain tracer 51, related information, including the identity of the subject corresponding to the test tube 1, the venue of the health checkup, the medical institution carrying out the health checkup, and the procedure of preserving the test tube 1 and transporting the test tube 1, can be recorded in the blockchain network 200. Since the related information can be traced but cannot be tampered with, the source and transportation history of the liquid 300 in the test tube 1 can be clearly recorded and managed. Therefore, the medical staff can trace the transportation history of the liquid 300 and thus trace quickly the subject's identity and liquid source by the aforesaid blockchain technology.

Figure 4:
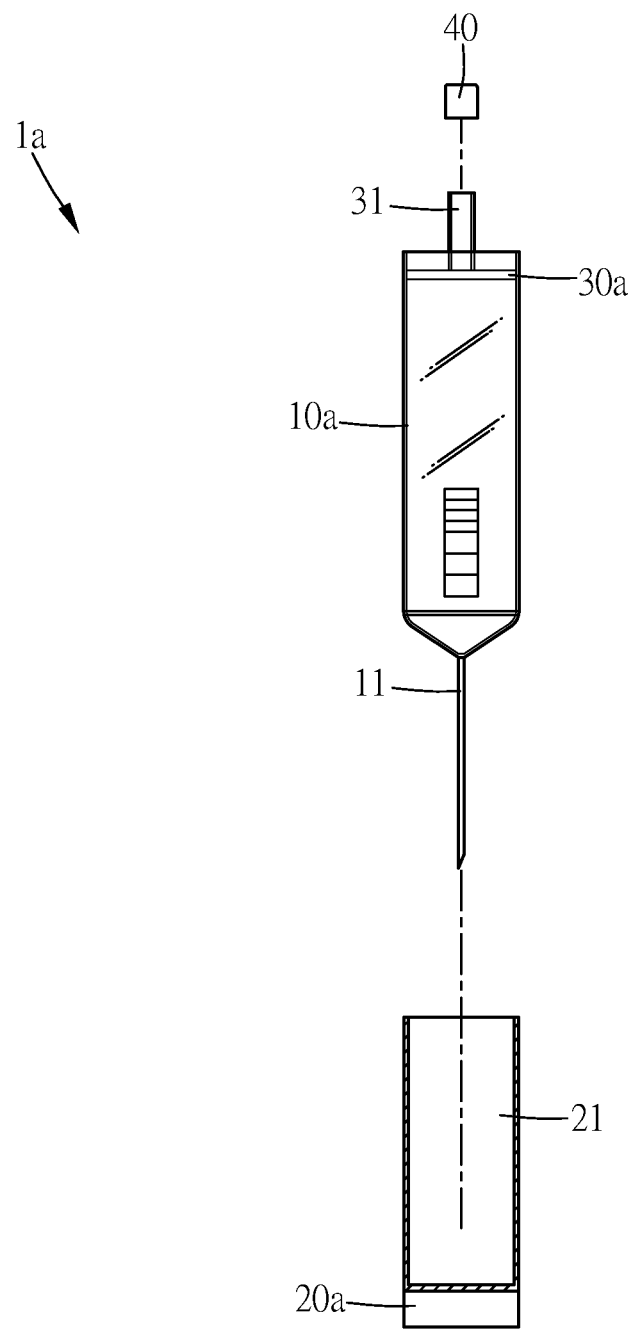
FIG. 4 is a schematic view of a test tube according to the second embodiment of the present disclosure.

Referring to FIG. 4, there is shown a schematic view of a test tube according to the second embodiment of the present disclosure.

As shown in FIG. 4, the difference between the second embodiment and the first embodiment is that, in the second embodiment, a tube body 10a of a test tube 1a further includes an injection needle 11. The injection needle 11 is disposed at the bottom of the tube body 10a. The bottom supporting element 20a further includes a supporting tube 21. The supporting tube 21 is a round tube and contains the injection needle 11 and supports the bottom of the supporting tube body 10a. The cover 30a is movably disposed at the top of the tube body 10a. Medical staff can remove the cover 30a to mount a piston core rod of an injector in place. Both the overlay unit 40 and the drip tube 31 of the cover 30a are in the number of one. Given the aforesaid structures, if the liquid contained in the tube body 10a is a vaccine, the vaccine can be directly injected into the human body with the injection needle 11 and piston core rod, whereas the tube body 10a can be vertically placed on the bottom supporting element 20a without pressing against the injection needle 11.

The test tube 1 of the present disclosure has diverse, convenient functions, namely, tracing the source and history of the liquid, positioning the test tube 1 in place to confirm the current position of the test tube 1, detecting the temperature of the test tube 1 to determine whether the temperature of the test tube 1 is appropriate, recording information of the test tube by radio frequency identification to allow medical staff to read the information quickly, and measuring the property of the liquid. In addition, the tube body is made of biodegradable plastic; consequently, the tube body is biodegradable and thus environment-friendly.

What is claimed is:

1. A test tube, for containing a liquid and electrically connected to a blockchain network, the test tube comprising:
   a tube body for containing the liquid;
   a cover disposed at a top of the tube body and comprising at least one drip tube;
   at least one overlay unit for covering the at least one drip tube;
   a chipset disposed on the tube body and comprising a blockchain tracer, the blockchain tracer recording a source of the liquid and a transportation history of the test tube in the blockchain network for tracing; and
   a detection module disposed on the tube body and electrically connected to the chipset, for measuring at least one liquid property of the liquid.

2. The test tube of claim 1, further comprising a bottom supporting element disposed at a bottom of the tube body.

3. The test tube of claim 2, wherein the chipset further comprises a positioning element for positioning the test tube in place.

4. The test tube of claim 3, wherein the chipset further comprises a temperature detecting element for detecting temperature of the test tube.

5. The test tube of claim 4, wherein the chipset further comprises an RFID tag for recording information of the test tube by radio frequency identification (RFID).

6. The test tube of claim 5, further comprising a wireless module disposed at the tube body and electrically connected to the chipset, the detection module and an external computer.

7. The test tube of claim 6, further comprising a battery disposed at the tube body and adapted to provide power to the chipset, the detection module and the wireless module.

8. The test tube of claim 7, wherein the tube body further comprises an injection needle, and the bottom supporting element further comprises a supporting tube for containing the injection needle.

9. The test tube of claim 8, wherein the tube body is made of biodegradable plastic.

10. The test tube of claim 9, wherein the positioning element is a global positioning system chip.

* * * * *